(12) United States Patent
Haller et al.

(10) Patent No.: US 6,922,176 B2
(45) Date of Patent: Jul. 26, 2005

(54) BELT COIL AS TRANSMITTER/RECEIVER ANTENNA IN A TRANSPONDER APPARATUS

(75) Inventors: Dirk Haller, Karlsruhe (DE); Harald Fischer, Weingarten (DE)

(73) Assignee: Forschungszenlrum Karlsruhe GmbH, Karlsruhe (DE)

( * ) Notice: Subject to any disclaimer, the term of this patent is extended or adjusted under 35 U.S.C. 154(b) by 26 days.

(21) Appl. No.: 10/751,029

(22) Filed: Jan. 2, 2004

(65) Prior Publication Data

US 2004/0140939 A1 Jul. 22, 2004

(30) Foreign Application Priority Data

Jan. 22, 2003 (DE) .......................................... 103 02 550

(51) Int. Cl.⁷ ................................................ H01Q 1/12
(52) U.S. Cl. ..................................................... 343/718
(58) Field of Search ................................. 343/718, 866

(56) References Cited

U.S. PATENT DOCUMENTS 4,817,196 A  *  3/1989  MacNak et al. .........  455/193.1
6,603,441 B2  *  8/2003  Teshima .....................  343/895
6,771,224 B2  *  8/2004  Apostolos ...................  343/718
6,788,262 B1  *  9/2004  Adams et al. ..............  343/718
2004/0212540 A1  *  10/2004  Kennedy et al. ............  343/718

* cited by examiner

Primary Examiner—Shih-Chao Chen
Assistant Examiner—Hung Tran Vy
(74) Attorney, Agent, or Firm—Klaus J. Bach

(57) ABSTRACT

In a belt coil serving as a transmitter/receiver for recording body-internal values, a belt coil including at least one insulated conductor tape for placement around a human or animal body part carries conductors and a connecting structure for closing the belt and interconnecting the individual conductors into a coil, and the belt tape includes a resilient section in which also each conductor is longitudinally expandable, and the contacts structures of the connector members are arranged in a displaced fashion such that the end of one conductor is connected to the beginning of a next adjacent conductor when the connecting members are joined and the opposite ends of the outermost conductors are accessible.

9 Claims, 9 Drawing Sheets

BELT COIL AS TRANSMITTER/RECEIVER ANTENNA IN A TRANSPONDER APPARATUS

BACKGROUND OF THE INVENTION

The invention relates to a belt coil as transmitter/receiver antenna in a transponder apparatus in human and veterinary medical apparatus.

For the recording of measuring data of medically interesting physiological parameters such as pressure, temperature, pH values etc, in connection with humans or animals, it is often important to gather these data over an extended period and as much as possible under normal living conditions, for example, in connection with a long time EKG. This is done so far in a way which is not satisfactory as far as the measuring technique is concerned particularly if the measurement values have to be derived from deeply within the body and cannot be derived directly from signals available at the skin surface, such as bladder pressure or brain pressure. In order to permit taking the measurements as much as possible under normal living conditions, the measuring equipment must not negatively affect the physiological functions and the comfort of the patient. The measuring equipment should therefore be such that it can be carried directly on the body or even be arranged within the body and it should be easy to service.

The biggest problem with such devices concerns the provisions for supplying the required operating energy. Inspite of substantial progress in minimizing the energy consumption of integrated circuits, even the most energy efficient microchips do not permit longtime measurements over periods of more than a few days or possibly weeks. Then the battery or accumulator of the measuring apparatus must be replaced. Because of the short servicing cycles such devices are not suitable for implantation in some depth within a body since each battery change would require a surgical procedure.

If, today, measuring data from deep within a human or animal body have to be collected over extended periods, the following procedure is employed:

The actual measuring value sensor is implanted into the body at the location where the value of interest is to be taken. The measurement value obtained by the sensor is then transmitted electrically for example by way of a cable or mechanically by way of a pressure measuring catheter to a measurement data processing apparatus which is disposed outside the body or implanted into the body just below the skin.

There is a tendency to arrange the measurement data processing apparatus not outside the body, but to implant them increasingly below the skin. The high integration density of modern semiconductor chips permits the arrangement of complex functions on a small chip. As a result, the processing systems for many applications are sufficiently small so that they can be implanted subcutaneously.

However, also subcutaneously implanted measurement data processing apparatus must be supplied with energy. A servicing procedure for changing the battery is in that case substantially less objectionable to the patient since only a superficial disturbance in the skin is needed to access the apparatus. Since, however, also this procedure is not suitable for use over extended periods such as several months or years the technique of inductively in-coupling energy through the skin for the charging of batteries in the measuring system was introduced.

But although with the inductive charging no invasive procedures are needed for the charging of the battery, this solution still has some drawbacks. An important disadvantage of all equipment where the measurement value sensor and the processing electronics are spatially separated resides in the cable connection which has to extend through several tissue layers of the body in order to interconnect both. For example, for measuring the pressure in the bladder, the bladder wall must be penetrated by the pressure sensor catheter or by the electrical connection to the sensor element and a distance to the nearest skin surface which in this case is the belly cover, must be bridged. On one hand, in this way, the tissue areas are irreversibly damaged because of the formation of scars or by tissue changes around the penetration channel of the connection and, on the other hand, the cable connection is subjected to constantly varying stresses as a result of the unavoidable movement of the tissue. Over an extended period, this results in material fatique and fracture of the cable whereby the implant is placed out of service.

In the transponder technology, including passive transponders, the transponder apparatus is supplied with energy and the collected information is removed therefrom over a certain distance by a portable or stationary reading apparatus. To this end, the transponder apparatus includes a transmission/receiving antenna which must be brought so close to the transponder that it is within reach of the electromagnetic alternating field. These antennas are actually coils providing for a magnetic coupling. The antenna coils may have various configurations; rectangular or round frame coils, rod coils, flat conductor plate coils, etc. All these configurations have in common that they are rigid and include a predetermined number of conductor windings.

For the use in the measurement of physical values in the body, these coils are not suitable since they do not adapt to the various body shapes in particular body areas. If a magnetic field is to be established within the area of the belly, the coil must be worn around the belly. In that case, firm support must be provided for the coil so as to prevent its slipping out of position. However, the coil must still be flexible and expandable so that freedom of breathing and movement of the patient are not restricted. Furthermore, it must be easy to install and remove the coil. The coil structure must also be comfortable to wear, at least it should be soft and flexible. Such properties are not provided with the antenna coils presently available.

A portable transmission and read-out antenna for measuring values in connection with a living person has become known so far only in one case. This is a system for measuring the material stresses of a hip joint prosthesis. In this case, a passive transducer in the interior of the head of the prosthesis was used. The read-out antenna was attached around the thigh at the level of the groin. In this experiment, for mounting, the antenna was tightly attached around the quadriceps so that it remained in place. In addition, it was fixed to the thigh by an adhesive tape. The antenna was neither flexible nor could it be opened or closed.

With the further development of the transponder technology particularly passive transponders without their own energy supply, a possibility has become available to eliminate the problems of measuring the physical body values as mentioned above. Passive transponders receive the energy needed for their operation from an alternating magnetic field to which they are exposed. From this field, they generate, by magnetic induction, the electrical voltage needed for their operation. Also, the data transmission occurs with the passive utilization of the alternating magnetic field in that the data are modulated onto the magnetic field by imposition on the induction coil in the transponder. Highly integrated microchips today combine the sensor technology for recording and preprocessing the sensor values with the electronic components for the passive transducer into a single component. In this way, it is possible to implant the complete measuring apparatus at the location in the body where the measurements are to be taken. Servicing is no longer necessary. Such a passive transducer could remain implanted for as long as it can serve a purpose.

It is the object of the present invention to provide a magnetically sensitive transmission and receiving arrangement which can be placed onto a human or animal body whereby a passive transponder implanted into the body can be supplied with energy and to which the transponder can supply information also by way of the magnetic field of the magnetically sensitive transmission and receiving arrangement. At the same time, wearing the antenna should not limit the movements of the wearer or limit them only in a bearable manner.

SUMMARY OF THE INVENTION

In a belt coil which serves as a transmitter/receiver for recording body-internal values, the belt which includes at least one insulated conductor tape for placement around a human or animal body part carries conductors and a connecting structure for closing the belt and interconnecting the individual conductors into a coil and the belt tape includes a resilient section in which also each conductor is longitudinally expandable, and the contact structures of the connector members are arranged in a displaced fashion such that the end of one conductor is connected to the beginning of a next adjacent conductor and the opposite ends of the outermost conductors are accessible.

The belt coil according to the invention can be worn like, or as, a normal belt, which can be closed and opened. It consists of at least one single-layer flat conductor of a length such that a predetermined area of a human or animal body can be fully surrounded in contact with that body part.

Such a flat conductor tape comprises at least one electrically insulated flexible conductor. If at least two such conductors are provided they are arranged parallel to one another.

At one or several locations of the flat conductor belt—depending on the application—an elastic support material is provided so as to extend in the longitudinal direction of the flat belt. On this support material, the conductor tape is supported in such a way that the conductor tape is wave-like contracted when tension on the elastic support material is relaxed. As a result, the conductor tape is extendable in the longitudinal direction and is adapted in this way, within limits, to different circumferences, that is, it can be used in connection with different-diameter body parts. As a result, the conductor tape, when worn, can adapt its length dynamically to the body of the wearer. The parallel support of the electrical conductors in the carrier mediums provides for uniform wave heights of the conductor tape within the elastic zone of the resilient materials.

The beginning and the end of the conductor tape are provided with contact buckles which can be interconnected and disconnected. The ends of the electrical conductors carry contact members, which are joined when the contact buckles are closed. With the buckle closed, the end of one conductor is in contact with the beginning of a next adjacent conductor. The beginning of the first outermost conductor and the end of the outermost conductor at the opposite side of the conductor tape are readily accessible in a single layer belt coil.

If the belt includes at least two conductor tapes disposed on top of one another, the contact buckles at the opposite ends of the belt have multi-layer contacts. In the layers of contacts, in addition to the conductor displacement structure in the plugs and, respectively, sockets of the buckle, for an end of an outer end conductor of the lower layer a contact is provided, upon connection of the buckle, with the beginning that is the first conductor in the next coil layer. With guide pins in the buckle parts the connecting procedure is safely guided such that the proper connections are established.

There are various embodiments for the guide structures which ensure the correct connection of the conductors upon closure of the connector buckle.

The opposite ends of the conductor tape are provided with a releasable and lockable device which establishes the conductive connection of the electrical conductors. Because of the design of the connecting element two connectors will be free no matter whether there is a single layer or multi-layer conductor structure. At the free connectors, the coil may be connected to a power supply and to a signal receiver and/or transmitter.

Upon closure, the two connector buckles are interlocked so that they cannot be disconnected unintentionally. The lock may be a locking engagement structure or it may be a clamp cup. In the elastic longitudinal section, the conductors are attached all in the same way to an elastic support structure by sewing, cementing or casting or clamping.

Because of the displaced interconnections of the conductors in the connector webs of the buckle, one of the connector webs includes two contacts which are accessible from the outside or there is one contact in each of the connector webs. Alternatively, one of the connector webs may be provided with a two-pole plug by way of which power can be supplied to the coil that is to the ends of the coil conductors thereof. Also data can be transmitted in the same way.

With this arrangement physical values of a living person or animal can be continuously measured at various parts of the body. Measurement possibilities are:

Measurements in the abdomen, bladder pressure, stomach pressure—with the coil tape as a belt;

Measurements of the head, brain pressure—the coil tape in the form of a head band;

Measurements at the arms and legs, stress measurements of the joint prosthesis and bones—coil tape in the form of a flexible band.

Below, the invention will be described in greater detail on the basis of the accompanying drawings.

DESCRIPTION OF A PREFERRED EMBODIMENT

Figure 1:
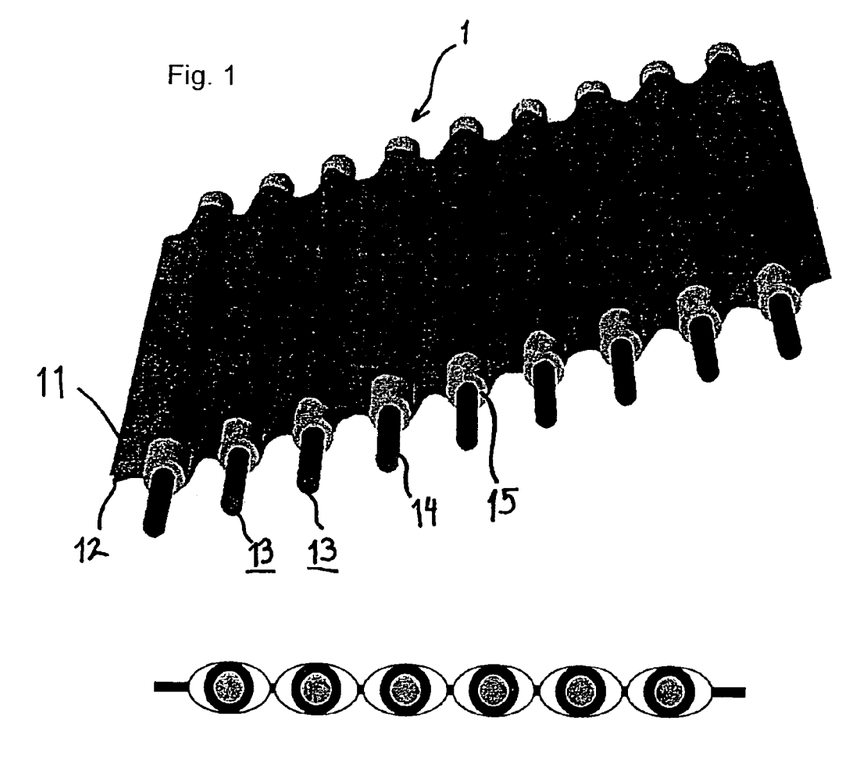
FIG. 1 shows a section of a single-layer conductor tape sewn into a material strap.

FIG. 1 shows a section of a single layer conductor tape. The parallel conductors 13 are disposed between two material strips 11, 12. The two material strips 11, 12 are sewn together along the longitudinal outer edges thereof and also between the conductors 13 and in this way retain the conductors 13. Instead of being sewn together, the material strips 11, 12 may also be glued together. Each individual conductor 13 comprises a copper wire 14 with an electrical insulation 15. Aluminum wires may also be used. They are advantageous particularly with a relatively large number of conductors as they have a lower weight. With an appropriate selection of the material for the strip with regard to electrical insulation properties, the conductor may not need a special insulation 15. In that case, the conductor tape would be relatively narrow and thin. Alternatively, a larger number of windings can be provided for a belt coil of the same width.

Figure 2:
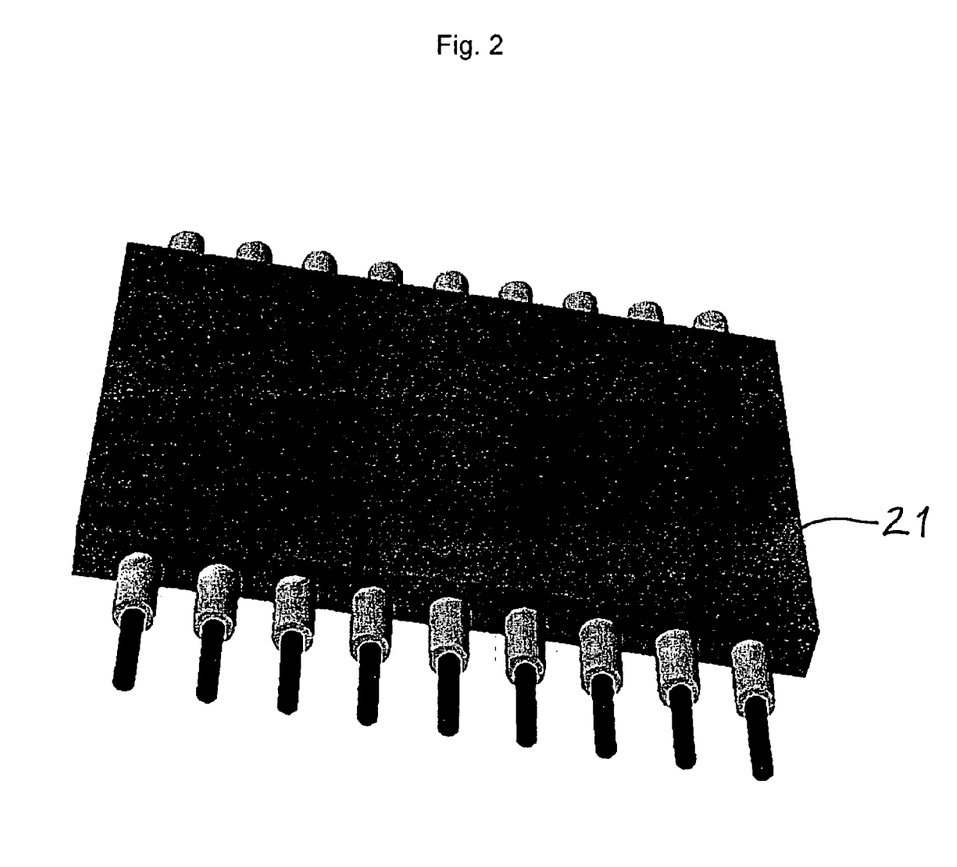
FIG. 2 shows a section of a single-layer conductor tape cast into a polymer band or belt.

FIG. 2 shows another embodiment of a conductor tape. In this case, a number of parallel conductors are molded into a polymer band 21. The conductors themselves are of the same construction as those described with reference to FIG. 1. This design is similar to a belt conductor. Also, in this case, wires without insulation may be used in order to save space or provide a larger number of wires.

Figure 3:
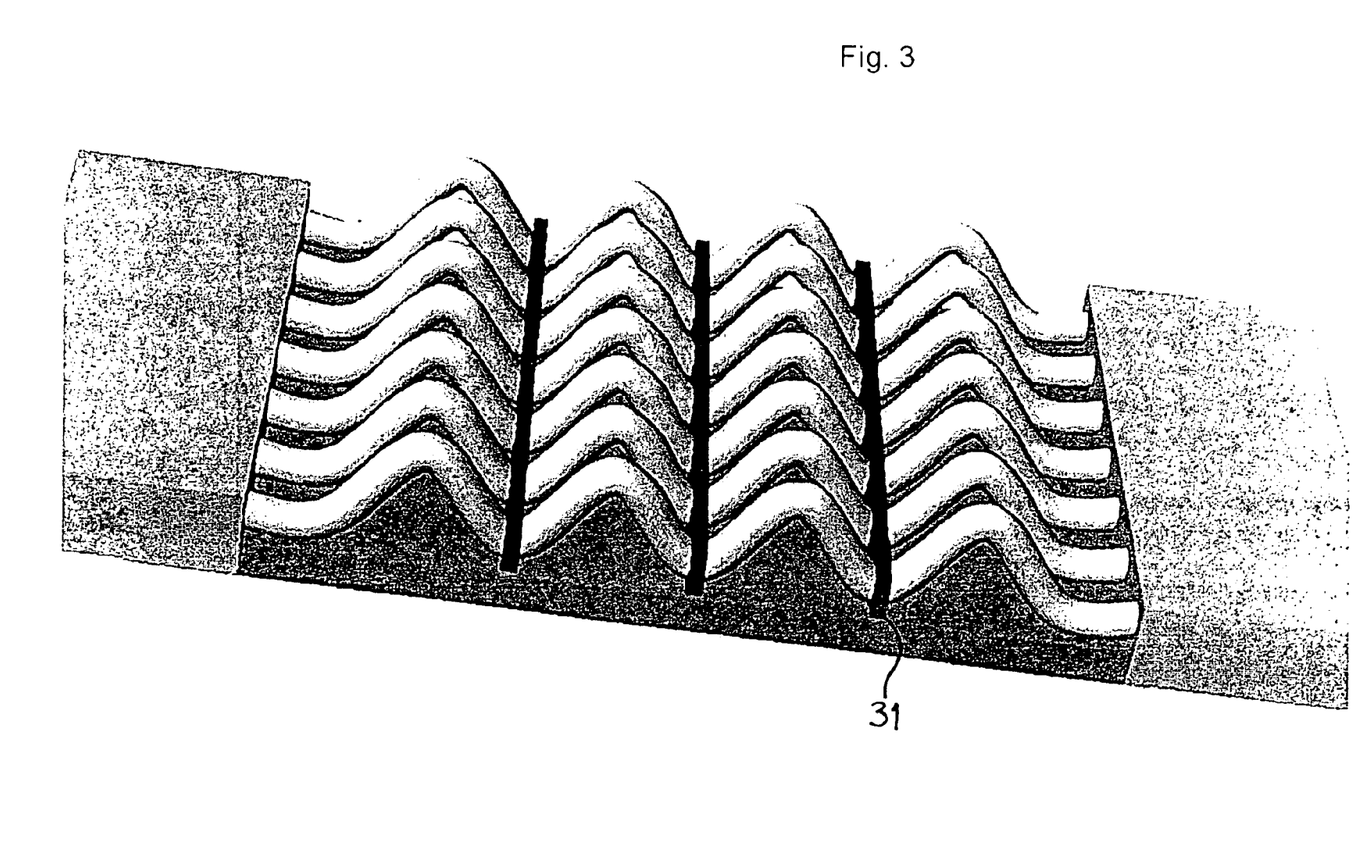
FIG. 3 shows an elastic section of a single-layer conductor tape, FIG. 4 a plug-in connector.

FIG. 3 shows a section of the belt coil which is elastic in a longitudinal direction. The representation shows the section in a relaxed state. In this case, the elasticity is achieved by a uniform extension of the conductors when the carrier tape is stretched. The corrugated arrangement of the conductors is achieved by sewing the conductors to the carrier tape only at the bottom of the wavy arrangement. However, the conductors may also be cemented to the carrier tape in these areas or by engagement with a comb-like web 31, which is fixed to the carrier tape. The conductors may also be fixed to the carrier tape by clamping. Altogether, these conductors are arranged in this section like subsequent wave fronts.

Figure 4:
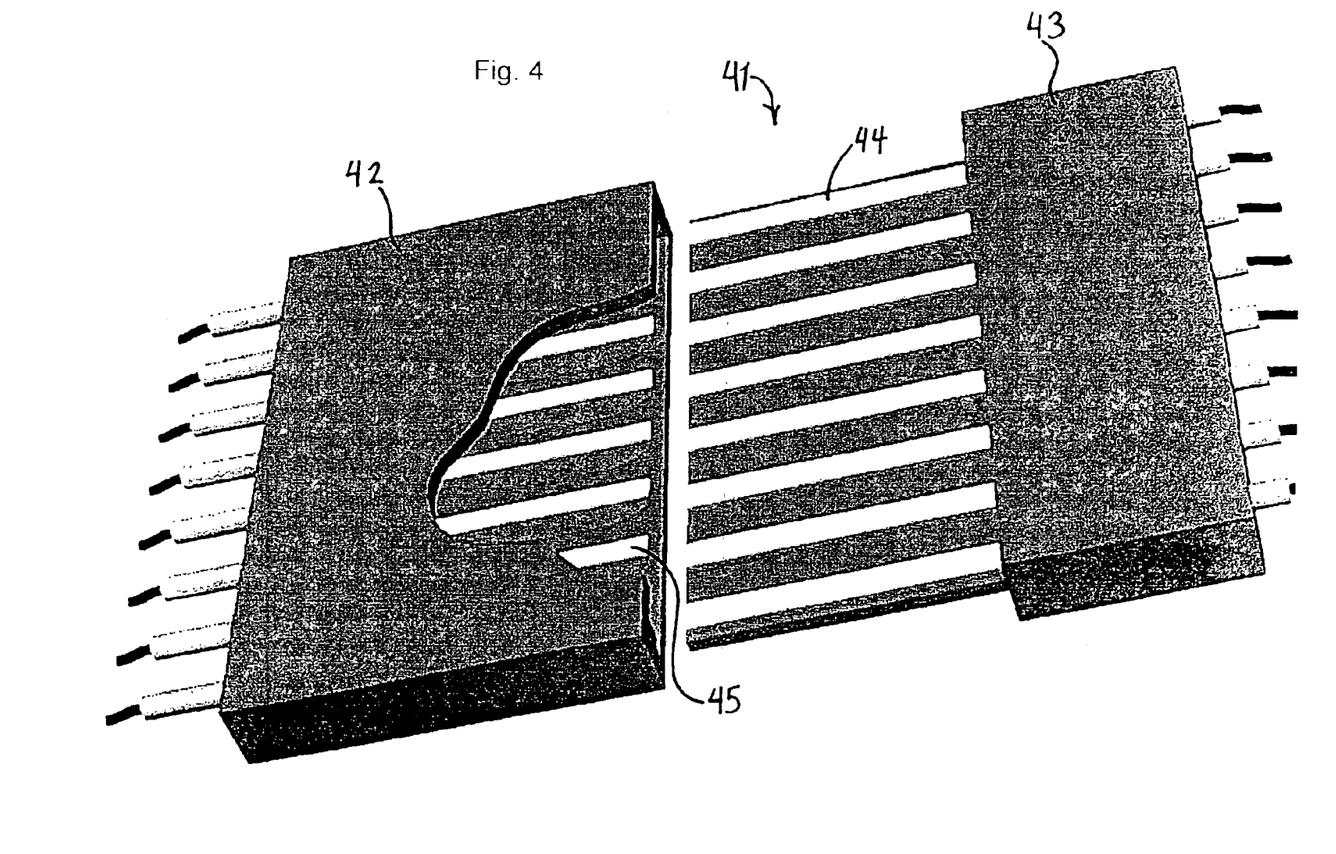

Important for the belt coil is the closure means or buckle 41, which includes two connector members, one at each end of the conductor tape. FIG. 4 shows the two connector members for a single-layer conductor structure with the two connector members disconnected. In the connector member 43, the contacts are knife blade contact members 44. The corresponding spring contacts 45 are disposed on the connector member 42. When the plug-type contact member 43 is inserted into the receptacle type connector member 42 the spring contacts 45 are biased resiliently onto the knife blade contacts 44. The displacement of a conductor end in the connectors is not shown in FIG. 4. This is rather shown in FIG. 9. FIG. 4 shows essentially-the knife blade contact arrangement, but other contact arrangements such as plug and receptacle contact arrangement may be used.

Figure 5:
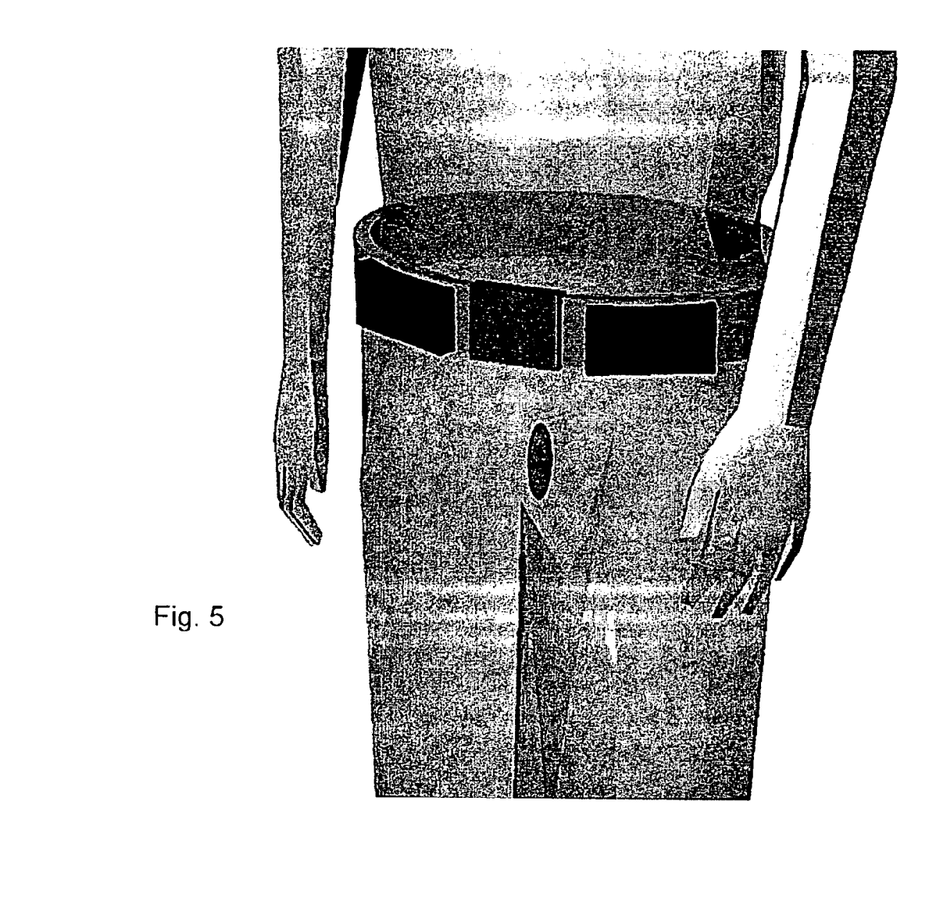
FIG. 5 shows an exemplary application of a belt-conductor for measuring the bladder pressure.

The example of a bladder internal pressure measurement is schematically shown in FIG. 5. The passive transducer is symbolized in the figure by the ellipse shown below the belt in the region of the bladder. The conductor belt extends around the body at the belt line like a buckled belt. With an appropriate design, the conductor belt is hardly distinguishable from a normal belt. It is certainly not recognizable as a medical-technical device. The representation shows, in addition to the connector buckle, devices at opposite sides of the conductor buckle which are arranged at the outside of the conductor belt. These include a battery carried along as a power supply and a control unit for reading the signals from the transducer disposed at the bladder.

Figure 6:
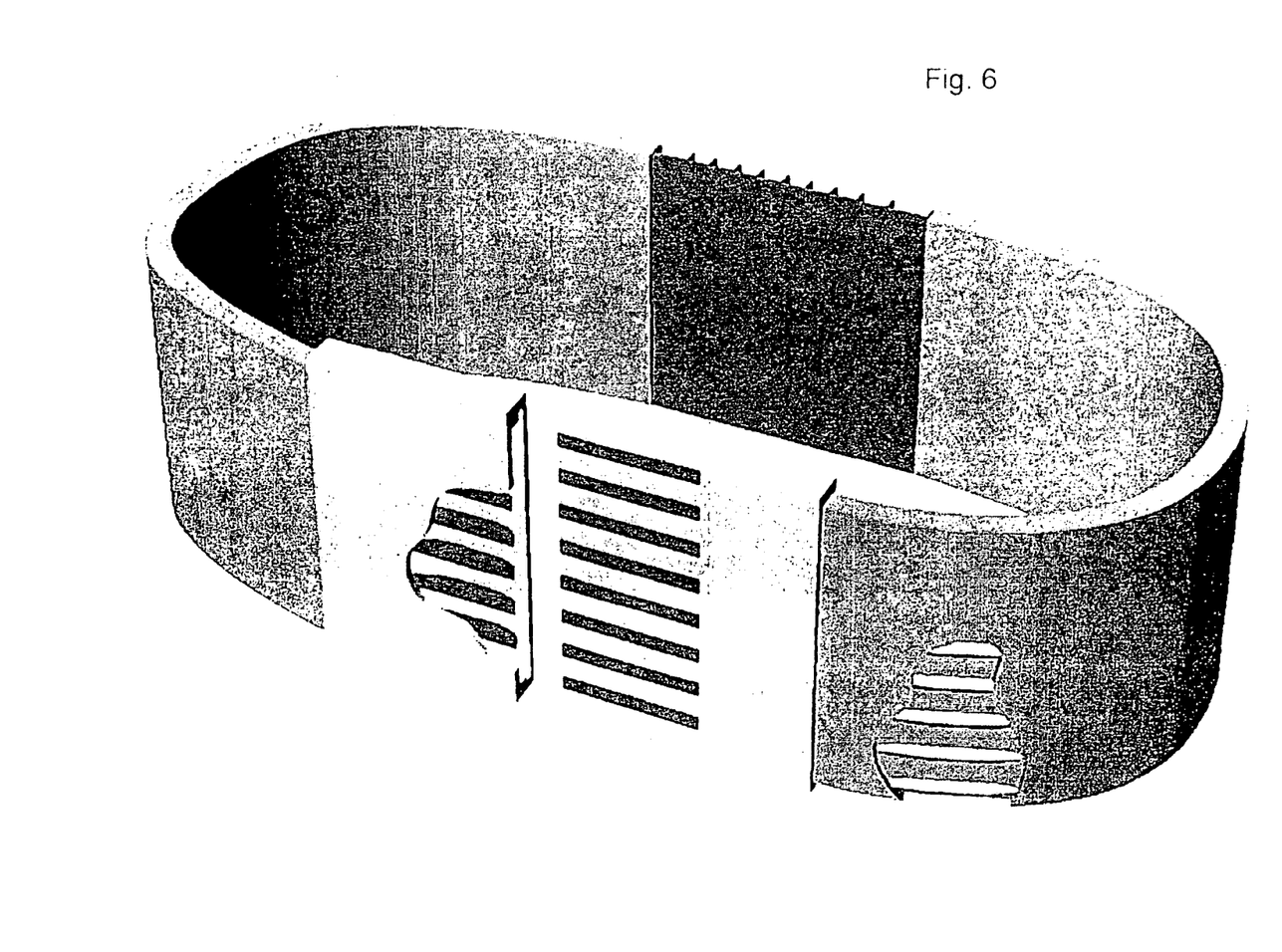
FIG. 6 is a front view of such a belt conductor showing particularly the connector belt knuckle.

FIG. 6 is a perspective view of the whole conductor belt showing its three essential features:

First, the belt connector with the two connector members shown closely adjacent each other but disconnected, Second, a single layer tape conductor, and Third, a longitudinally elastic section at the backside of the belt.

Figure 7:
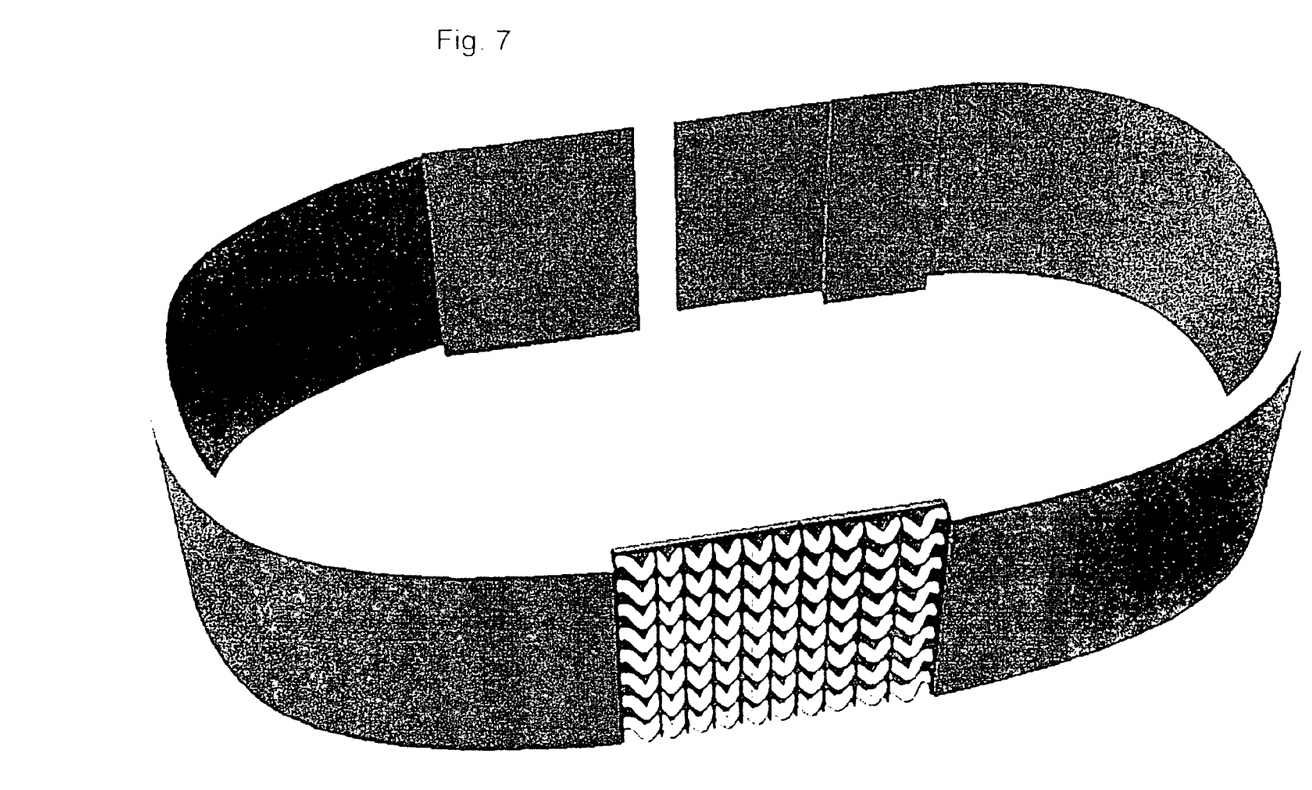
FIG. 7 shows the belt conductor from the rear.

FIG. 7 shows the conductor belt of FIG. 6 from the rear where the wave front-like arrangement of the conductors in the longitudinally elastic section are seen in a relaxed state.

Figure 8:
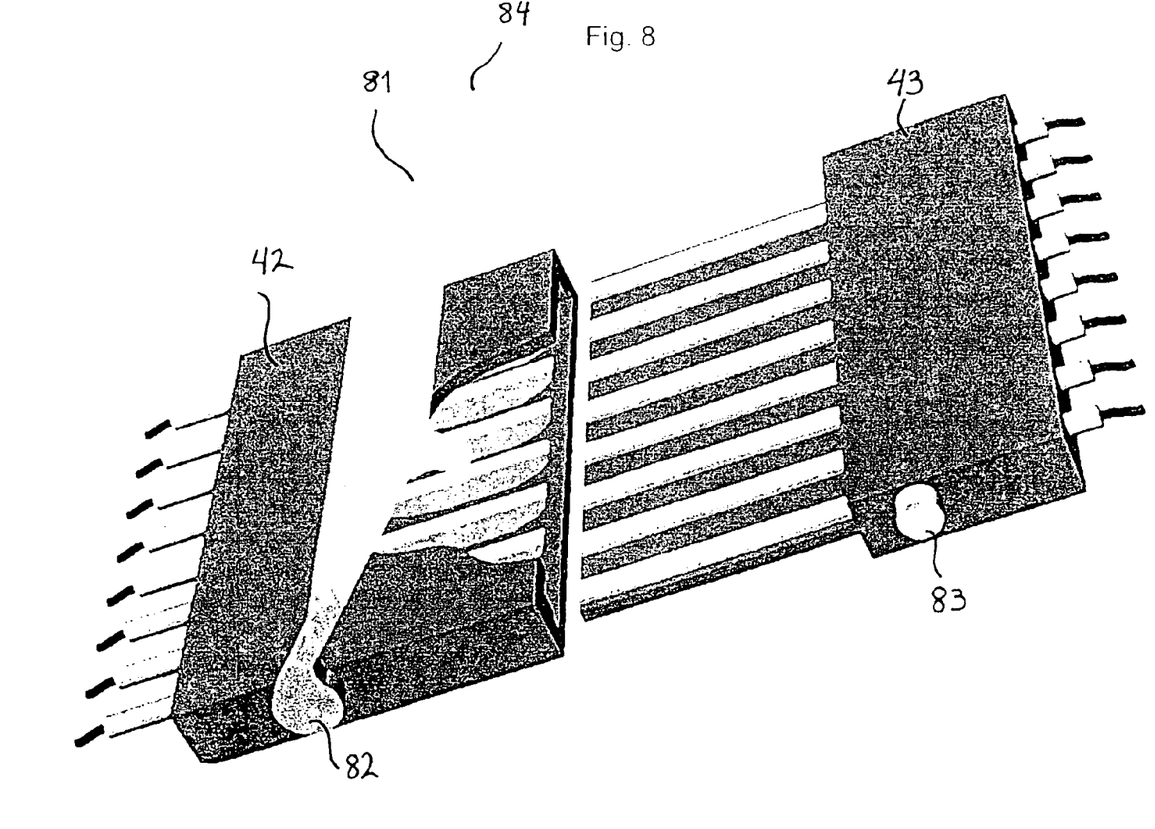
FIG. 8 shows a connector lock.
Figure 9:
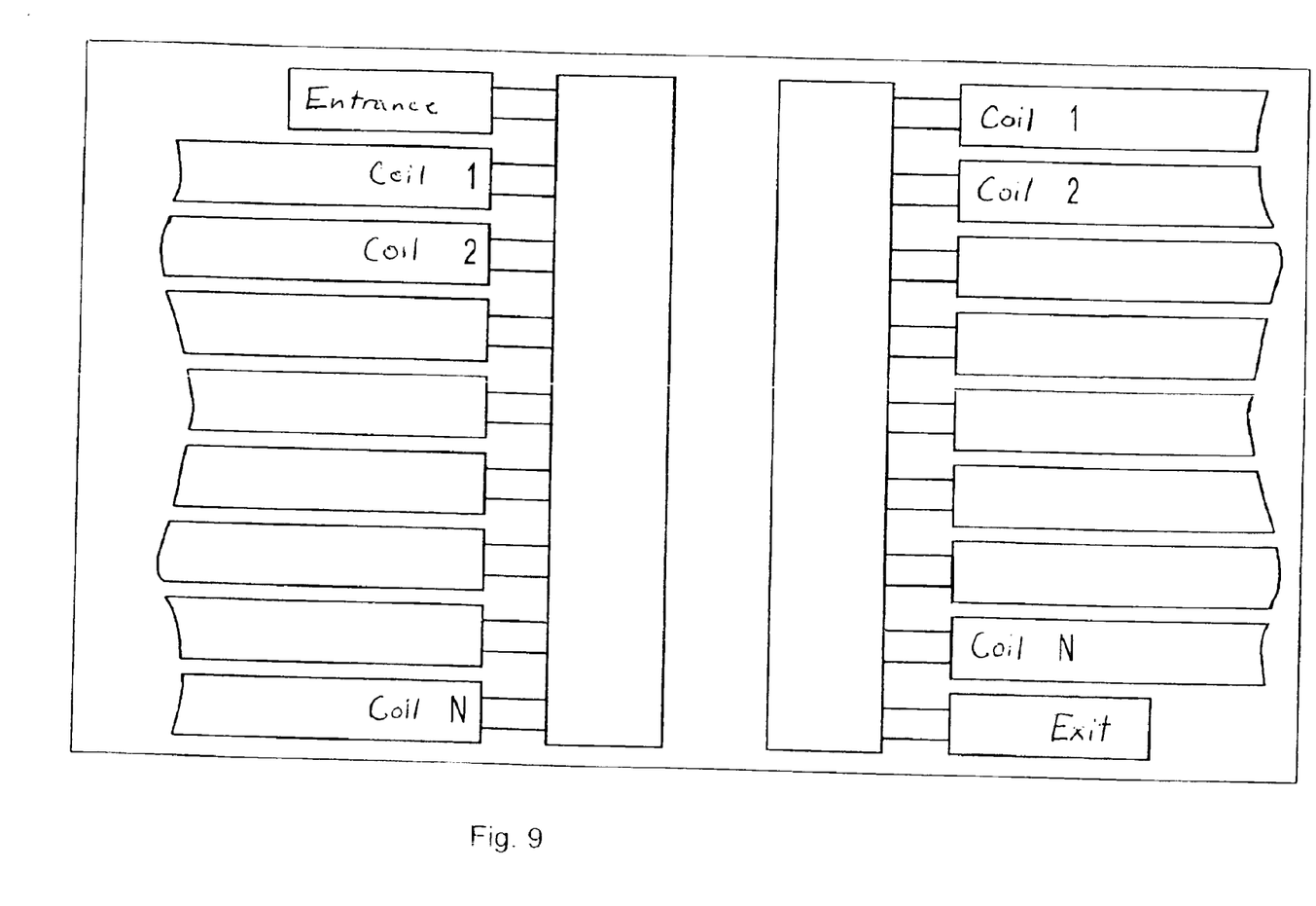
FIG. 9 shows the conductor displacement.

FIG. 8 shows a locking structure for the belt connector or connector belt buckle with a locking arm 81 which is pivotally supported by the connector member 42 at a pivot support 82. The connector member 43 is provided with projections 83 and the locking arm is provided at its end with an engagement hook 84 by which the projection 83 can be firmly engaged when the connector member 43 is fully inserted into the connector member 43. Then the two connector members are safely interlocked, and cannot be unintentionally disconnected. However other locking means such as a VELCRO® lock may be used FIG. 9 shows a conductor displacement structure, which can be provided with simple contactor webs. In this case, a single layer connector is provided with n parallel individual conductors. Each of the connector members 42, 43, however has (n+1) contacts. The beginning of the coil formed by the conductors is at the left hand connector member 42 at the upper first contact strip 91, so that, upon insertion of the connector 43 into the contact member 42, electrical contact is established between the first contact strip 91, which is the beginning of the coil and the contact strip 92 of the connector member 43. The contact strip 92 is connected to the conductor 92, which extends in the conductor tape to the second contact strip 94 of the connector member 42. This scheme is repeated for all the subsequent conductors up to the end of the $n^{th}$ winding which is the end of the coil and is connected to the $(n+1)^{th}$ contact 95 of the connector member 42 and also of the connector member 43. Other connector arrangements known in the art could of course also be used if they are suitable for the particular application. The shown embodiment however is simple and easy to manufacture and therefore economical.

What is claimed is:

1. A belt coil as a transmitter/receiver antenna in a transponder apparatus for medical and veterinary applications, comprising: a belt coil having at least one electrically insulated conductor tape of a length such that it can be placed tightly around a human or animal body part, said conductor tape including at least one electrically insulated flexible conductor extending on said tape in parallel arrangement with any additional conductor, said conductor tape including a resilient section and each conductor being longitudinally expandable along the resilient section of said conductor tape, a connector member provided at each of the opposite ends of said conductor tape, said connector members being insertable into, and lockable in engagement with, each other, said connector members including contact structures which are joined when the connector members are interconnected, and said conductors being connected to said contact structures in a displaced fashion such that the end of one conductor is transposed to join the beginning of the next transversely adjacent conductor, and the beginning of the first conductor as well as the end of the last conductor are accessible.

2. A belt coil according to claim 1, wherein said belt coil includes at least first and second layers of conductors and the beginning of the second layer of conductors is connected to the end of the last conductor of first layer of conductors, the end of the last conductor of the second layer of conductors being accessible.

3. A belt coil according to claim 1, wherein said connector members include locking means for interlocking said connector members in a connected state.

4. A belt coil according to claim 3, wherein said locking means is a releasable engagement lock.

5. A belt coil according to claim 3, wherein said locking means is a hook and loop lock.

6. A belt coil according to claim 3, wherein said locking means includes a locking arm pivotally supported on one of said connector member and engageable with said other connector member for preventing unintended disconnection of said connector member.

7. A belt coil according to claim 1, wherein said conductors are connected to the elastic tape section by one of sewing cementing or clamping.

8. A belt coil according to claim 7, wherein each of said connector members includes a single-pole connector with a contact wire to the respective free conductor end of the connector member providing electrical access to the beginning and the end of the coil formed with the connector members closed.

9. A belt coil according to claim 7, wherein one of said connector members includes a double pole connector with contacts to the free conductor ends of the connector members so as to provide for electrical access to the beginning and the end of the coil formed with the connector members closed.

* * * * *